United States Patent
Fischetti et al.

[11] Patent Number: 5,944,756
[45] Date of Patent: Aug. 31, 1999

[54] MODULAR PROSTHESIS WITH OFFSET ATTACHMENT MECHANISM

[75] Inventors: Gary Fischetti, Franklin; David Sheehan, Carver, both of Mass.

[73] Assignee: Johnson & Johnson Professional, Inc., Raynham, Mass.

[21] Appl. No.: 08/200,118

[22] Filed: Feb. 22, 1994

[51] Int. Cl.⁶ .............. A61F 2/28; A61F 2/30; A61F 2/38

[52] U.S. Cl. .............. 623/18; 623/16; 623/18; 623/20

[58] Field of Search .............. 623/16, 18, 20

[56] References Cited

U.S. PATENT DOCUMENTS

| | | | |
|---|---|---|---|
| 4,822,366 | 4/1989 | Bolesky | 623/20 |
| 4,950,297 | 8/1990 | Elloy et al. | 623/20 |
| 4,985,037 | 1/1991 | Petersen | 623/16 |
| 5,002,581 | 3/1991 | Paxson et al. | 623/18 |
| 5,137,535 | 8/1992 | Keller | 623/23 |
| 5,152,796 | 10/1992 | Slamin | 623/20 |
| 5,326,359 | 7/1994 | Oudard | 623/20 |
| 5,330,534 | 7/1994 | Herrinton et al. | 623/20 |

*Primary Examiner*—Mickey Yu
*Assistant Examiner*—Alvin Stewart
*Attorney, Agent, or Firm*—Joseph F. Shirtz

[57] ABSTRACT

A modular prosthesis attachment mechanism which uses a special bolt that provides an attachment position that is not directly over the hole or recess used to capture the head of the bolt. Thus, the attachment mechanism can be used with one location hole on a prosthesis and provide multiple augmentation locations just by offering multiple bolts with varying offsets. The use of a washer-like support may also be required to help redistribute the forces associated with the new attachment location. Thus, the invention is beneficial in knee replacement surgery requiring augmentation pieces. By providing the surgeon with a number of options to best place each piece, such as a stem, this mechanism can be helpful in meeting the needs of individual patients.

7 Claims, 2 Drawing Sheets

MODULAR PROSTHESIS WITH OFFSET ATTACHMENT MECHANISM

FIELD OF THE INVENTION

The present invention relates to a modular knee prosthesis system, that is, a system of implantable prosthesis used to replace a natural knee and which includes a series of attachment means which permit attachment of an anchoring stem in different locations.

Background of the Invention

Total knee prosthesis have been in use for some time. These prostheses generally comprise a tibial component, a femoral component and a patellar component. The femoral component of the prosthesis generally comprises spaced-apart condylar portions and a connection joining the condylar portions. The tibial component of the prosthesis is constructed to receive the condylar portions of the femoral component, that is, the condylar portions are in direct contact and are supported by the tibial component. The femoral contact surface of the tibial component is made from a biocompatible plastic material such as ultra-high molecular weight polyethylene. The patellar portion of the prosthesis is generally ultra-high molecular weight polyethylene which may be metal-backed or reinforced and which is affixed to the natural patella and rides in a depression on the metal surface of the femoral component. Typical of such prosthesis is the prosthesis shown in U.S. Pat. No. 4,298,992, the disclosure of which is incorporated herein by reference. The prosthesis of the type shown in the above-mentioned patent are generally available with or without an intramedullary stem. The intramedullary stem is used to lend lateral stability to the prosthesis and is inserted into the medullary canal of the femur. The stems are set at an angle to the vertical which duplicates the valgus angle in the human anatomy. The valgus angle is the angle between the center line of the femur and an imaginary vertical line extending from the distal femur to the center of the femoral head. The angle is generally somewhere between 5° and 9°. Often in the course of knee-replacement surgery it is necessary to provide augmentation in order to support the prosthesis evenly across the attachment. In order to place this augmentation at the most preferred location, it has been found that current prosthesis when attached, for example, to a distal femoral portion, may need to be repositioned.

For example, U.S. Pat. No. 5,152,796 shows a significant advance in the design of modular knee prosthesis. The prosthesis disclosed in that patent uses a series of specially designed stems and bolts in order to provide variability to the valgus angle of the prosthesis. In this way, a single main prosthesis element may have stems attached thereto which would make the prosthesis appropriate for either the right or left knee and at varying valgus angles.

SUMMARY OF THE INVENTION

The present invention provides for a modular knee system, in particular, a system wherein a stem is attached to an articulating surface. By provision of at least two different bolts having different degrees of offset, the spacial position of the stem may be selected during the surgery by merely assembling the various components using a preselected offset bolt positioning the stem at the location required by the surgeon.

The articulating component forms an outer surface which has defined thereon two condylar surfaces. These surfaces mimic the condyles of the natural knee and are common in knee prostheses. The two condylar surfaces are joined by an intercondylar portion. The intercondylar portion further defines an opening therethrough.

The bolts of the present invention are provided having different offsets. For example, one bolt may have no offset and merely be a straight connecting bolt, and a second bolt may be offset slightly or to a variable degree. That is, an entire family of modular bolts may be provided having different degrees of offset in order to permit a significant number of locations of the stem. By offset, it is intended that generally the position of the head of the bolt is spaced from the longitudinal axis of the remainder of the bolt portion (for example a threaded portion). Thus the offset permits the location of the bolt head in the same opening while the remainder of the shaft and threads are positioned at a different location depending on the offset of the bolt.

Each of the bolts is adapted to be connected to and fitted into the opening defined in the inter-condylar portion. Once fitted within this opening, a selected bolt extends upward from a superior surface of the articulating component at a position which is predetermined by the surgeon in fixed spacial relationship to the outer articulating surface.

An implantable femoral stem is received on the bolt by way of female threads provided at one end of the stem. In this manner the bolt is inserted into the opening defined previously and a stem is threaded thereon. Thus the position of the stem at its root or base is defined by the offset of the bolt and is positioned to be extending from the superior surface of the articulating component once attached.

A washer may be provided in order to spread the forces of the butt engagement of the stem on the superior surface of the articulating component. That is, the provision of multiple offsets creates the need for a large contact area for the stem. However the stem position is not ultimately known until the bolt is inserted. Thus the provision of a washer between the stem and the superior surface of the articulating component permits spreading of the forces of engagement between the stem and the articulating component.

Alternatively, the stem may be flared at one end (i.e., the root or butt) in order to provide a widened contact area for contact with the superior surface of the articulating component. In this manner, the washer described above is effectively built in to the stem and provided in order to spread the forces over a more compatible area.

DETAILED DESCRIPTION OF THE INVENTION

The figures depict solely a femoral component of a knee prosthesis system. Generally the prosthesis may be of a type similar to those known in the art and include appropriate patella and tibial components.

Figure 1:
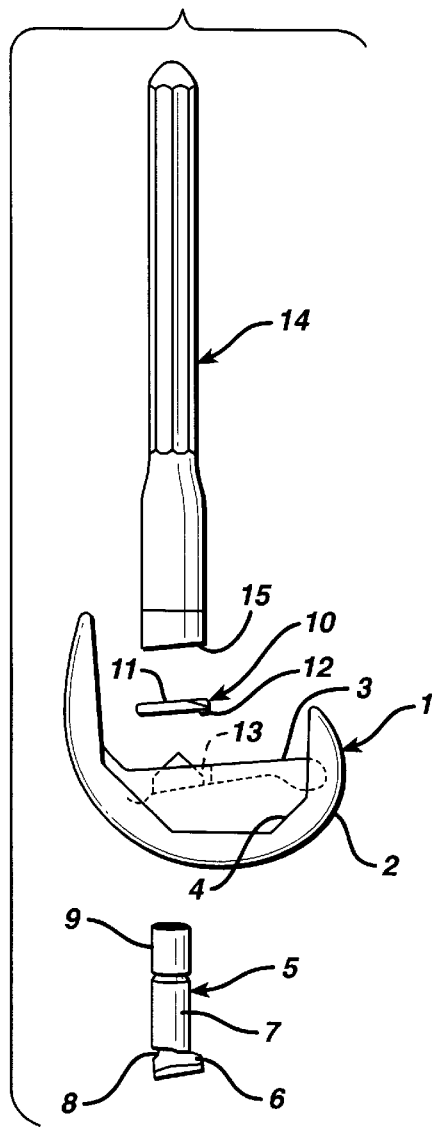
FIG. 1 is an exploded view of a prosthesis of the invention.

Referring now to FIG. 1, there is shown a first embodiment of the invention. A knee prosthesis 1 is shown having an outer condylar surface 2. The prosthesis is actually formed with two condylar surfaces in a known manner.

However, the condylar surface of the present figure is shown for reference purpose only. The knee prosthesis 1 has a superior surface 3 which in a portion forms chamfers 4. These chamfers ride along appropriate cuts or augmentation devices of a properly prepared distal portion of a femur.

A bolt 5 is formed of a head 6 and body 7. The head 6 and body 7 of the bolt 5 are connected via a neck 8 which is offset slightly. That is, the head extends slightly to one side of the main access of the body. For example, the body may be cylindrical in shape and therefore define a longitudinal cylindrical axis which axis is offset from the center axis of the head 6. The bolt 5 has a threaded portion 9 which may be threaded either internally or externally. The threaded portion 9 meets with an appropriate complimenting threaded portion of the stem which will be described below.

A washer 10 is provided having an opening 11 passing therethrough. The washer 10 is formed such that its opening 11 is offset from a central access of the washer. That is, the washer compliments the offset neck of the bolt described above. The opening, rather than being cylindrical, may have a sloping portion in order to compliment the offset nature of the bolt 5. A tab or tang 12 depends from the bottom of the washer 10 and in the assembled position is received within a slot 13 formed in the superior surface 3 of the knee prosthesis 1. In this way, the washer is positioned on the superior surface 3 of the knee prosthesis 1 with its offset positioned properly to receive the bolt 5 and reposition the stem 14.

Figure 2:
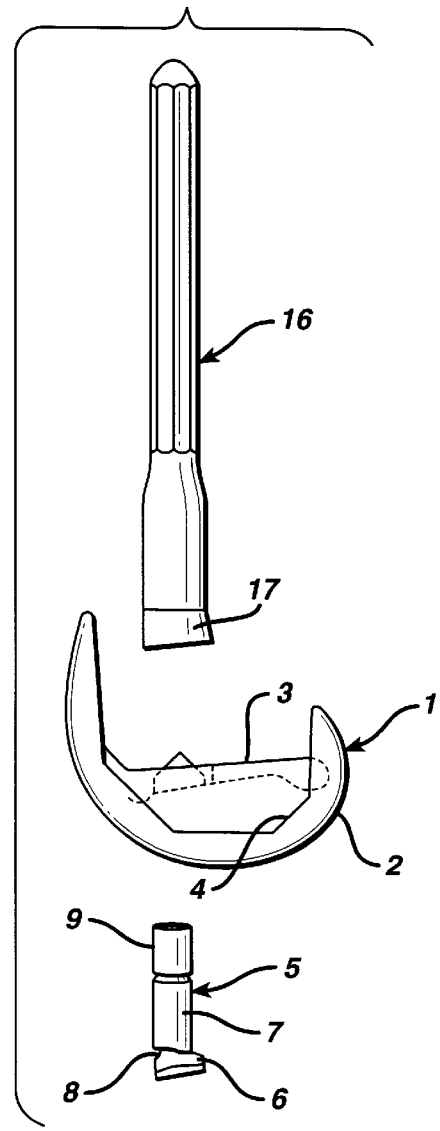
FIG. 2 is an exploded view of an alternative embodiment of the prosthesis of the present invention.

The stem 14 of the present embodiment is of a type substantially known in the prior art. That is, it is merely a straight stem provided with appropriate attachment means to receive the threaded portion 9 of the offset bolt 5. The stem 14 is threaded onto the bolt 5 until inferior end 15 is mated firmly against the washer 10. Thus, the washer 10 is sandwiched between the inferior end 15 of the stem 14 and the superior surface 3 of the knee prosthesis 1. In the embodiment depicted in FIG. 2, the knee prosthesis 1 and bolt 5 are substantially the same as the embodiment described above. In this alternative embodiment, the offset stem 16 is constructed such that a washer 10 (as shown in the previous embodiment) is not necessary. The offset stem 16 has a flare 17 which extends slightly to one side so as to mate the inferior end 15 with the superior surface 3 of the knee prosthesis 1. The washer 10 and flare 17 of the two described embodiments are present in order to assure that a portion of the stems 14 and 16 seats firmly on a solid surface. In the case of the first embodiment, the stem 14 seats solidly on the washer 10 which in turn seats solidly on the superior surface 3. In the alternate embodiment, the flare 17 provides sufficient area to mate completely with superior surface 3.

Figure 3:
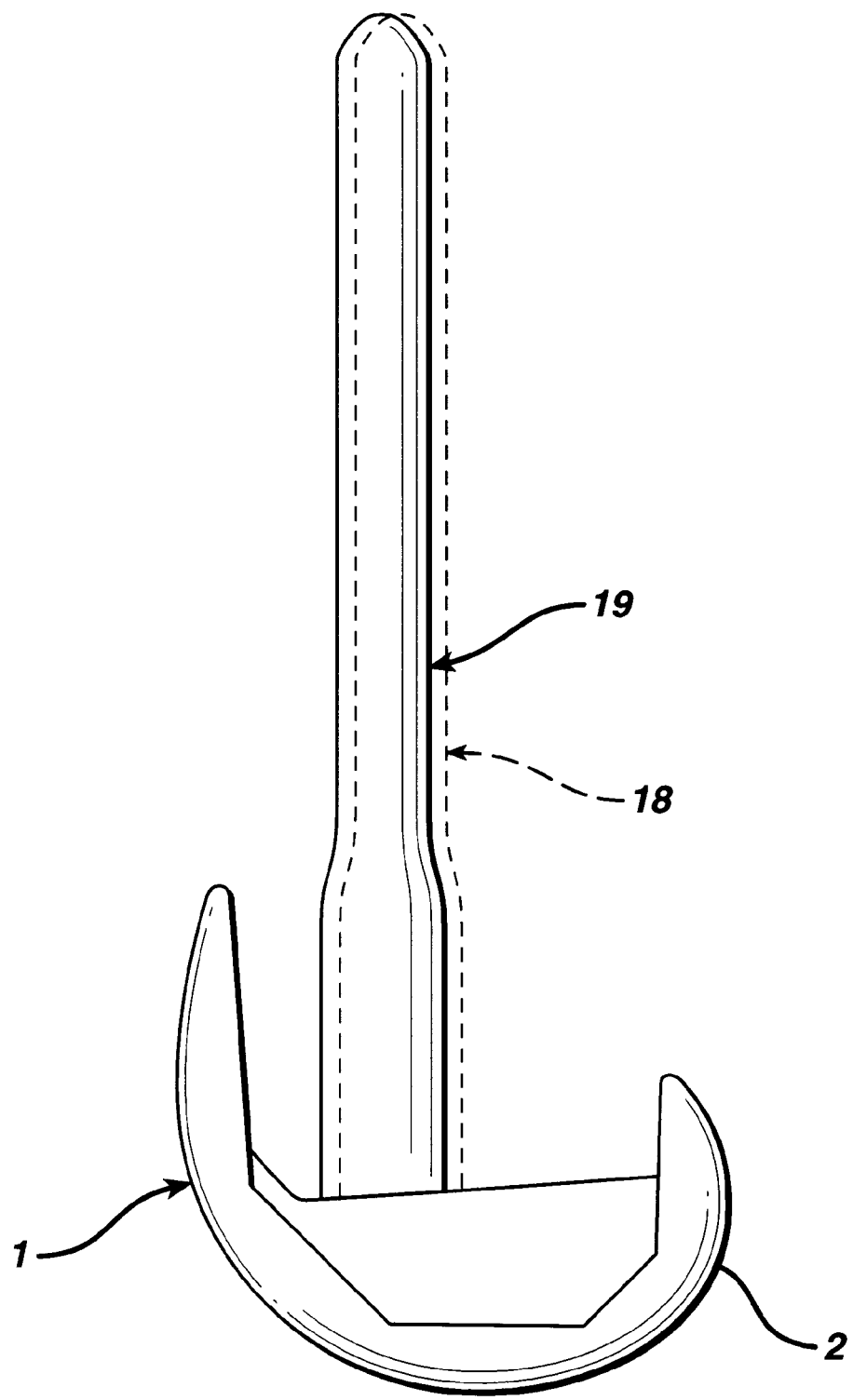
FIG. 3 is a partially schematic view of a prosthesis of the present invention showing the multiple locations of the prosthesis stem.

Thus, in either event, the stem of the present invention is moved as depicted in FIG. 3. In FIG. 3 the broken-line position 18 shows the prior are stems wherein the bolt was not offset. In those devices the bolt was inserted through the opening formed in the prosthesis and the stem threaded down into tight engagement with the prosthesis. However, the position on the prosthesis at which the stem was mounted was not adjustable. However, with the offset bolt of the present invention the stem may be positioned in an offset position 19 as shown in FIG. 3 or any variation thereof for which a bolt is supplied. Thus, in the present invention a system of prosthesis with modular stem attachment is provided merely by providing multiple offset and non-offset bolts for locating the terminal position of the inferior surface of the stem.

The invention will now be described with reference to the attached claims. It should be understood that the device may be varied from the claims without avoiding the spirit and scope of the present invention.

What we claim is:

1. A modular femoral component for a knee system comprising:

a) an articulating component forming an outer surface having two condylar surfaces joined by an intercondylar portion, said intercondylar portion defining an opening therethrough;

b) at least two bolts having a shaft and a head, one of said bolts having said shaft offset from said head different from at least one other bolt, each of said bolts adapted to be connected to and fitted into said opening with the bolt extending upward from a superior surface of said articulating component at a position in fixed spacial relationship to said outer surface determined by said offset; and c) an implantable, femoral stem received on said bolt and extending from said superior surface at said fixed spacial position.

2. A modular femoral component as claimed in claim 1 wherein the offset of the bolt ranges from 0 to 5 mm.

3. The modular femoral component as claimed in claim 1 wherein said stem has a flared inferior end which mates with the superior surface of the articulating component.

4. The modular femoral component as claimed in claim 1 further comprising a washer of a diameter wider than a diameter of said stem for receipt between said stem and said superior surface to provide a firm interface between said stem and said superior surface.

5. The modular femoral component as claimed in claim 4 further including positioning means on said washer.

6. The modular femoral component as claimed in claim 5 wherein said washer defines an opening for receiving said bolt and said opening follows the offset of the bolt.

7. The modular femoral component as claimed in claim 6 wherein said positioning means includes a tab depending from a surface of said washer.

\* \* \* \* \*